United States Patent
Wear et al.

(10) Patent No.: US 11,826,188 B2
(45) Date of Patent: Nov. 28, 2023

(54) SYSTEM AND METHOD FOR IMAGING A SUBJECT

(71) Applicant: GE Precision Healthcare LLC, Wauwatosa, WI (US)

(72) Inventors: James A. Wear, Madison, WI (US); Adam Manders, Madison, WI (US); Mehadi Hassan, Madison, WI (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 202 days.

(21) Appl. No.: 17/513,719

(22) Filed: Oct. 28, 2021

(65) Prior Publication Data
US 2023/0136752 A1    May 4, 2023

(51) Int. Cl.
*A61B 6/00* (2006.01)
*G06T 7/00* (2017.01)

(52) U.S. Cl.
CPC ............ *A61B 6/505* (2013.01); *A61B 6/4078* (2013.01); *A61B 6/4233* (2013.01); *A61B 6/482* (2013.01); *A61B 6/488* (2013.01); *A61B 6/5205* (2013.01); *A61B 6/5217* (2013.01); *A61B 6/5241* (2013.01); *A61B 6/545* (2013.01); *A61B 6/589* (2013.01); *G06T 7/0012* (2013.01); *G06T 2207/30008* (2013.01)

(58) Field of Classification Search
None
See application file for complete search history.

(56) References Cited

U.S. PATENT DOCUMENTS

| | | | |
|---|---|---|---|
| 6,081,582 A | 6/2000 | Mazess | |
| 6,496,557 B2 | 12/2002 | Wilson | |
| 6,584,171 B2 * | 6/2003 | Suzuki | A61B 6/548 348/E5.088 |
| 6,807,249 B2 * | 10/2004 | Dinten | A61B 6/482 378/54 |
| 7,336,763 B2 * | 2/2008 | Spartiotis | H04N 23/698 378/38 |
| 7,634,061 B1 | 12/2009 | Tuemer | |
| 8,165,266 B2 | 4/2012 | Wear | |

(Continued)

*Primary Examiner* — Thomas R Artman

(57) ABSTRACT

The present disclosure relates to a medical imaging system having an X-ray source, a detector and a processing system. The the X-ray source is collimated to produce a diverging beam of radiation and transmits X-rays through an object. The detector includes detector pixels arranged in at least one row and is operative to receive the X-ray energy of the X-rays after having passed through the object. The processing system is programmed to select an initial height of the object with respect to the X-ray source plane and determine an initial time delayed summation (TDS) shift frequency based on the initial height. The processing system performs a first scan of the object based on the TDS shift frequency and determines a new height of the object based on a beam angle and an overlap of adjacent images. A new TDS shift frequency is determined based on the new height of the object if the initial height and the new height are not substantially same. The processing system then performs a second scan of the object based on the new TDS shift frequency. The processing system is further programmed to generate an image of the object based on detected X-ray energy at the X-ray detector based on the first scan and the second scan.

20 Claims, 11 Drawing Sheets

(56) References Cited

U.S. PATENT DOCUMENTS

| | | | |
|---|---|---|---|
| 8,774,354 B2 | 7/2014 | Ullberg | |
| 10,499,873 B2* | 12/2019 | Wear | A61B 6/4035 |
| 10,743,825 B2* | 8/2020 | Bruno | A61B 6/542 |
| 2001/0021244 A1* | 9/2001 | Suzuki | H04N 25/711 |
| | | | 348/E5.088 |
| 2001/0048732 A1* | 12/2001 | Wilson | A61B 6/4233 |
| | | | 378/54 |
| 2003/0026385 A1* | 2/2003 | Dinten | A61B 6/482 |
| | | | 378/98.9 |
| 2006/0203959 A1* | 9/2006 | Spartiotis | A61B 6/14 |
| | | | 378/38 |
| 2009/0290680 A1* | 11/2009 | Tumer | G01T 1/247 |
| | | | 250/311 |
| 2011/0058649 A1* | 3/2011 | Wear | A61B 6/505 |
| | | | 257/E31.015 |
| 2012/0014503 A1* | 1/2012 | Ullberg | H04N 25/711 |
| | | | 378/19 |
| 2015/0190102 A1* | 7/2015 | Bruno | A61B 6/542 |
| | | | 378/39 |
| 2018/0168533 A1* | 6/2018 | Wear | A61B 6/482 |
| 2019/0000407 A1* | 1/2019 | Muller | A61B 6/505 |
| 2019/0150863 A1* | 5/2019 | Bruno | A61B 6/542 |
| 2020/0163643 A1* | 5/2020 | Desaute | A61B 6/4233 |
| 2021/0204892 A1* | 7/2021 | Wear | A61B 6/032 |
| 2023/0136752 A1* | 5/2023 | Wear | A61B 6/5205 |
| | | | 378/62 |

* cited by examiner

SYSTEM AND METHOD FOR IMAGING A SUBJECT

BACKGROUND

The subject matter disclosed herein relates generally to medical diagnostic imaging systems, and more particularly to a system and method for acquiring patient bone images.

Dual-energy imaging systems such as a bone densitometer includes an x-ray source that emits a collimated beam of dual-energy x-rays to image a patient. An x-ray detector is positioned with respect to the x-ray source to receive the x-rays passing through the patient. The x-ray detector produces electrical signals in response to the received x-rays. The electrical signals are converted to digital signals that are utilized by the imaging system to generate images of the patient.

Measurements of the x-ray absorption by an object at two different x-ray energies can reveal information about the composition of that object as decomposed into two selected basis materials. In the medical area, the selected basis materials are frequently bone and soft tissue. The ability to distinguish bone from surrounding soft tissue allows x-ray images to yield quantitative information about in vivo bone density for the diagnosis of osteoporosis and other bone disease.

Current bone densitometers use frame-based data acquisition methods to scan patients. In this mode the use of highly-pixellated 2-D detectors generates large volumes of data with typically low x-ray statistics per pixel that complicates image reconstruction. Therefore, there is a need for an improved system and method to acquire bone density information.

BRIEF DESCRIPTION

In accordance with an embodiment of the present technique, a medical imaging system having an X-ray source operative to transmit X-rays through an object is provided. The X-ray source is collimated to produce a diverging beam of radiation. The medical imaging system also includes a detector operative to receive the X-ray energy of the X-rays after having passed through the object, wherein the detector includes detector pixels arranged in at least one row and a processing system. The processing system is programmed to select an initial height of the object with respect to the X-ray source plane and determine an initial time delayed summation (TDS) shift frequency based on the initial height. The processing system is also programmed to perform a first scan of the object based on the TDS shift frequency and determine a new height of the object based on a beam angle and an overlap of adjacent images. The processing system is further programmed to determine a new TDS shift frequency based on the new height of the object if the initial height and the new height are not substantially same and perform a second scan of the object based on the new TDS shift frequency and generate an image of the object based on detected X-ray energy at the X-ray detector based on the first scan and the second scan.

In accordance with another embodiment of the present technique, a method for imaging an object is provided. The method includes providing an X-ray source operative to transmit X-rays through an object and providing a detector operative to receive the X-ray energy of the X-rays after having passed through the object. The X-ray source is collimated to produce a diverging beam of radiation. The method also includes selecting an initial height of the object with respect to the X-ray source plane and determining an initial time delayed summation (TDS) shift frequency based on the initial height. A first scan of the object is performed based on the TDS shift frequency and further a new height of the objected is determined based on a beam angle and adjacent images overlap. The method further includes determining a new TDS shift frequency based on the new height of the object if the initial height and the new height are not substantially same and performing a second scan of the object based on the new TDS shift frequency. Finally, the method includes generating an image of the object based on detected X-ray energy at the X-ray detector based on the first scan and the second scan.

In accordance with yet another embodiment of the present technique, a medical imaging system having a multi-energy X-ray source operative to transmit X-rays through a patient is provided. The X-ray source is collimated to produce a diverging beam of radiation. The medical imaging system further includes a detector operative to receive the X-ray energy of the X-rays after having passed through the patient and a processing system. The detector includes detector pixels arranged in at least one row. The processing system is programmed to perform a scan of the patient based on a time delay summation (TDS) frequency and to generate at least two images of a patient bone corresponding to the multi-energy levels of the multi-energy X-ray source. The processing system is further programmed to determine a patient bone mineral density (BMD) based on the at least two images.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

Exemplary embodiments of dual-energy x-ray systems and methods for acquiring, for example bone and tissue information are described in detail below. In particular, a detailed description of an exemplary dual-energy x-ray system will first be provided followed by a detailed description of various embodiments of methods and systems for generating patient anatomy images that may be used to diagnose a medical condition such as osteoporosis for example. In one embodiment, the system and method may be used for acquiring and measuring bone mineral density, bone tissue information, and other bone related information from patient bone images. In another embodiment, the system and method may be used for determining body composition which distinguishes lean and fat tissue in regions which do not contain bone.

At least one technical effect of the various embodiments of the systems and methods described herein is to acquire accurate patient anatomy such as bone images using a dual-energy x-ray imaging system. In some embodiments, a single dual-energy x-ray scan, and more particularly, a single body scan is used to acquire image information for a number of different bones, from which bone lengths are determined.

Figure 1:
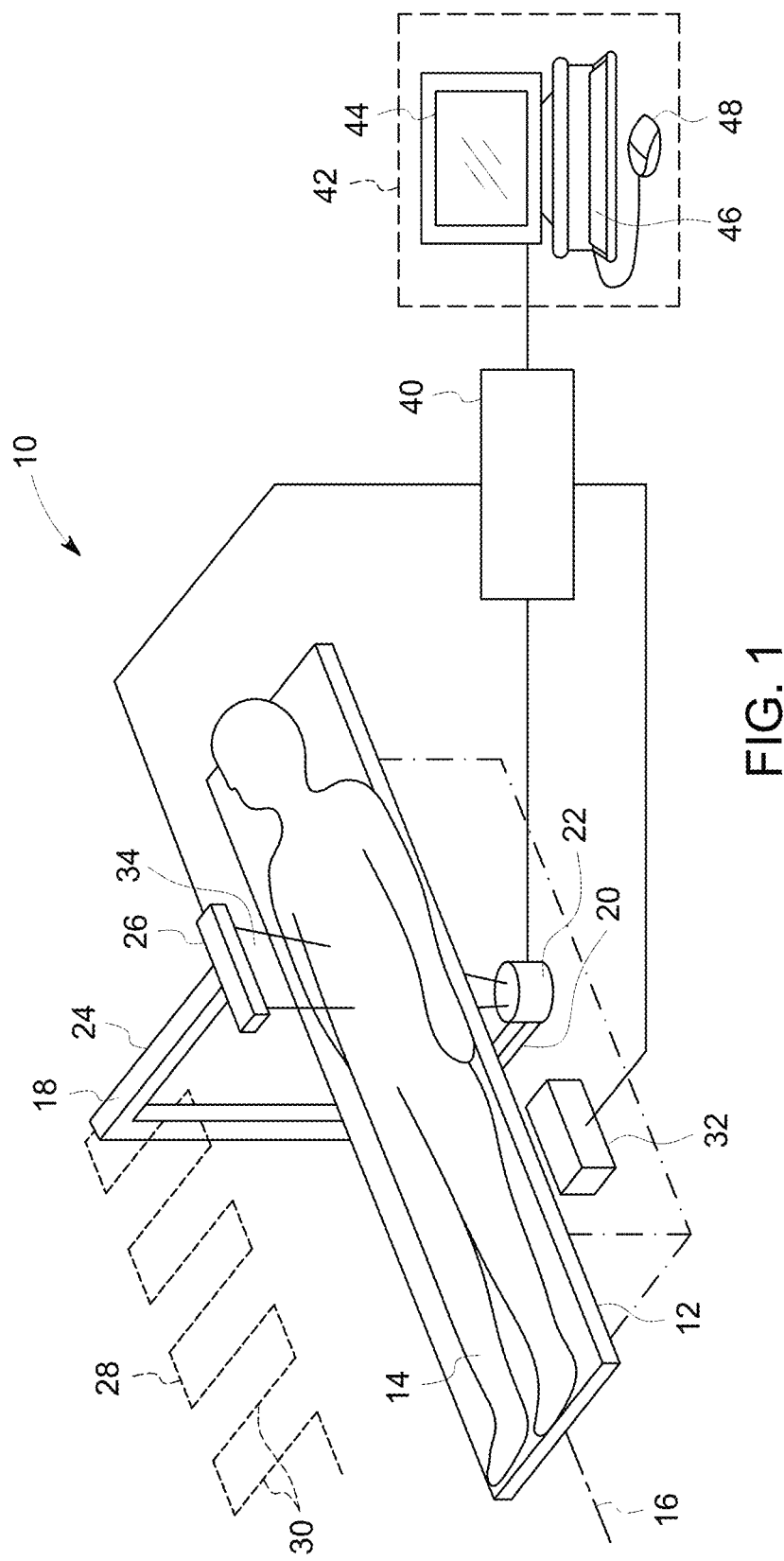
FIG. 1 is a schematic diagram of a dual-energy x-ray imaging system illustrating a full body scan, in accordance with an embodiment of the present technique.

FIG. 1 is a schematic diagram of an exemplary dual-energy x-ray system, illustrated as a dual x-ray absorptiometry (DEXA or DXA) system 10, which is also referred to as dual energy bone densitometer system capable of performing bone densitometry. The system 10 constructed in accordance with various embodiments is configured to measure at least an area of a bone, a length of a bone, a bone mineral content (BMC), a bone mineral density (BMD), and a tissue thickness or density. The BMD is calculated by dividing the BMC by the area of the bone. During operation, an x-ray beam with broadband energy levels is utilized to scan a subject, for example, to scan a human subject to image the bones of the human subject. The acquired images of the bones are used to diagnose a medical condition such as osteoporosis. The images may be generated in part from determined bone density information acquired during a dual-energy x-ray scan.

The system 10 includes a patient table 12 providing a horizontal surface for supporting a subject, for example, a patient 14 in a supine or lateral position along a longitudinal axis 16. The system 10 also includes a support member, for example, a C-arm 18. The C-arm 18 has a lower end 20 that is positioned beneath the patient table 12 to support an x-ray source 22. The C-arm 18 has an upper end 24 that is positioned above the patient table 12 supporting an x-ray detector 26. Optionally, the x-ray detector may be coupled to the lower end 20 and the x-ray source 22 coupled to the upper end 24. The x-ray detector 26 may be fabricated, for example, as a multi-element cadmium-tellurium (CdTe) detector providing for energy discrimination. The x-ray source 22 and the x-ray detector 26 may be moved in a raster pattern 28 so as to trace a series of transverse scans of the patient 14 during which dual energy x-ray data is collected by the x-ray detector 26. The transverse scanning procedure generates either a single image or quantitative data set, from a plurality of scan images acquired across a patient, wherein the x-ray source 22 and the detector 26 are either longitudinally aligned with the superior-inferior axis of the patient or transversely from the patient's left to right. Scanning a patient using a transverse motion facilitates minimizing the time between acquisitions of adjacent scan images because the transverse direction across the patient is shorter than the longitudinal direction across the patient. Thus, transverse scanning can reduce the severity of patient motion artifacts between scan images allowing the images to be more accurately merged.

The transverse scanning motion is produced by actuators (not shown) under control of a translation controller 32. During operation, the x-ray source 22 produces a fan beam 34 having a plane that is parallel to the longitudinal axis 16. Optionally, the fan beam 34 may have a plane that is perpendicular to the longitudinal axis 16. The raster pattern 28 is adjusted such that there is some overlap (e.g., slight overlap of 10 percent) between successive scan lines of the fan beam 34. The x-ray source 22, the x-ray detector 26, and the translation controller 32 communicate with, and are under the control of, a computer which may include both dedicated circuitry and one or more processors having the ability to execute a stored program.

Referring again to FIG. 1, the computer 40 communicates with a terminal 42 including a display 44, a keyboard 46, and a cursor control device such as a mouse 48 allowing for operator input and the output of text and images to the operator. In some embodiments, the computer 40 is located remotely from the workstation 42. Optionally, the computer 40 may form a portion of the workstation 42. The computer is adapted to perform one or more processing operations. The acquired bone and tissue information, for example, image and density information may be processed and displayed in real-time during a scanning session as the data is received. Additionally or alternatively, the data may be stored temporarily in a memory device on the computer 40 during a scanning session and then processed and displayed in an off-line operation. The information may also be stored in a long-term storage device (e.g., hard-drive or server) for later access, such as during a follow-up scan of the same patient and useful to monitor, for example, the change in bone and tissue density over a period of time. The display 44 includes one or more monitors that present patient information, including the scanned image and the bone length images to the operator for diagnosis and analysis. The displayed images may be modified and the display settings of the display 44 also manually adjusted using the keyboard 46, the mouse 48, or a touch screen icon on the display itself.

During operation, the system 10 is configured to operate in either a dual energy x-ray mode or a single energy x-ray mode. In the single energy mode, the x-ray source 22 emits x-rays at a narrow band of energies of a few keV and in the diagnostic imaging range of approximately 20-150 keV. In the dual-energy mode, the x-ray source 22 emits radiation at two or more bands of energy emitted simultaneously or in rapid succession. The x-ray source 22 may also be configured to emit a single broadband energy of more than a few keV over the diagnostic imaging range. The system 10 may be switched between the dual energy mode and the single energy mode by increasing or decreasing the x-ray source 22 voltage and/or current. The system may also be switched between the dual energy mode and the single energy mode by removing or adding a K-edge filter. It should be noted that the x-ray source 22 may emit x-rays at different energies or ranges of energies.

The x-ray source 22 may be configured to output a fan beam of x-rays 34 as shown in FIG. 1. In some embodiments, the computer 40 controls the system 10 to operate in the single energy mode or dual-energy mode to determine the bone or tissue information of at least some of the scanned body. The single energy mode generally enables higher resolution images to be generated. The acquired images may then be used to measure, for example, bone density or other bone and tissue characteristics or content. As discussed above, the dual-energy x-ray scan may be a rectilinear scan of the entire patient body, which may be performed in a transverse-type scanning sequence as described above. During the dual-energy x-ray scan an image of the entire body of the patient may be acquired, which includes image information relating to the bones and tissue in the body. The full body or total body scan of the entire body may be performed as a single scanning operation, which may be a low dose mode scan. In some embodiments, instead of a full body or total body scan, individual rectangular regions of the body may be performed, which may be single sweep scans. Once the scan of the patient, or a portion thereof, is completed, the dual energy signals provided by the detector 26 are deconstructed into images of two basis materials, such as bone and soft tissue. The high and low energy signals can also be combined to provide a single energy mode having superior signal to noise ratio for imaging purposes.

The detector 26 shown in FIG. 1 may be embodied as either a linear array of detector elements, a side linear array of detector elements, which includes two transversely separated rows of detector elements, or a stacked array detector in which the detector elements are stacked along a direction of propagation of the radiation and are selectively sensitive to low and high energy spectrums, respectively.

Figure 2:
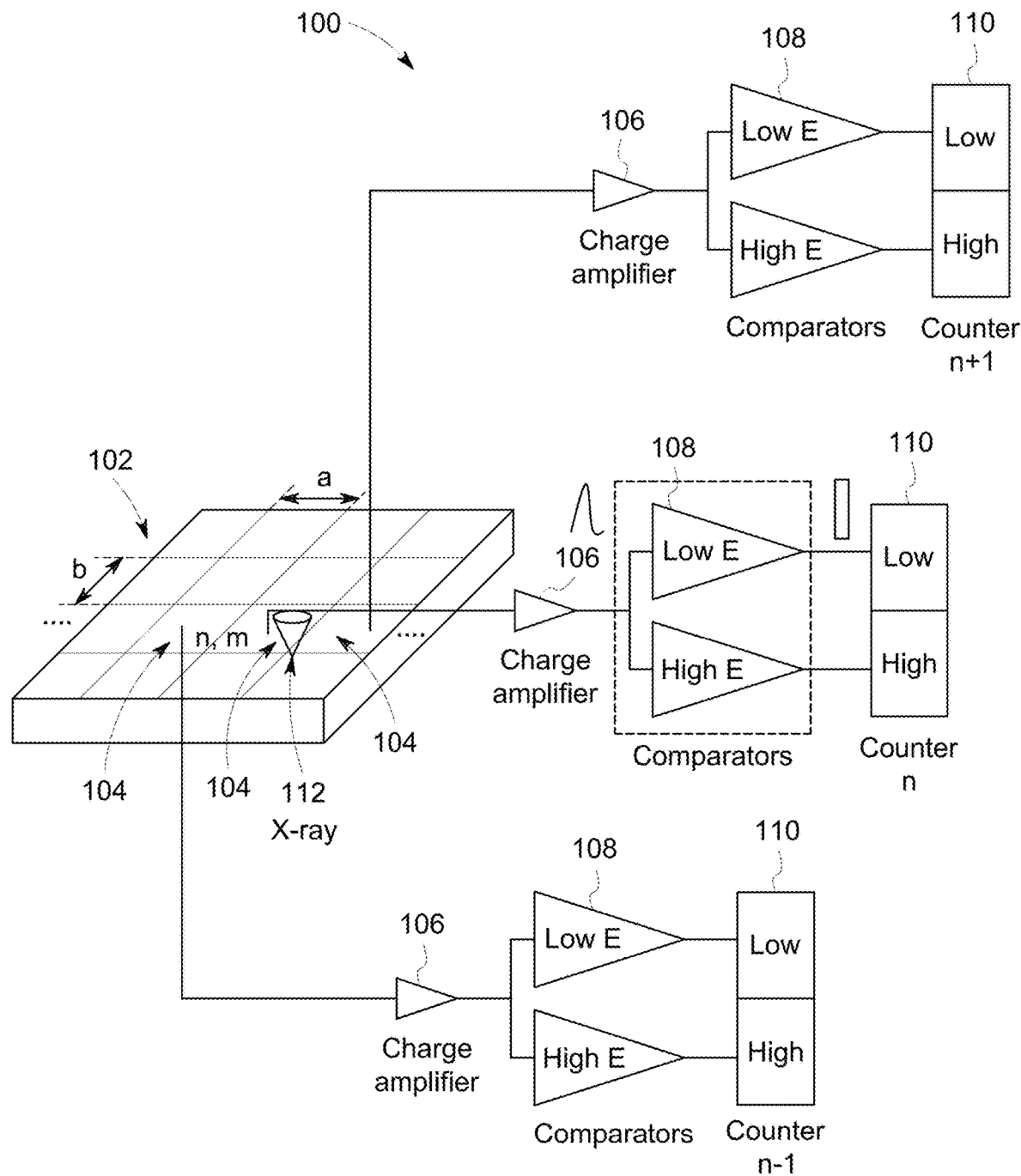
FIG. 2 is a schematic diagram of a detector and related circuitry used in FIG. 1, in accordance with an embodiment of the present technique.

FIG. 2 depicts a schematic diagram 100 of a detector and related circuitry used in system of FIG. 1. In general, schematic diagram 100 shows a detector 102 which can be used as detector 26 of FIG. 1. The detector 102 includes an array of detector pixels 104 having n rows and m columns. Each of these detector pixels are connected to a charge amplifier 106, one or more comparators 108 and a counter 110. When the x-ray beam 112, after passing through a subject or the patient, hits a particular detector pixel (e.g., pixel (n, m)), the detector pixel (n, m) converts the x-ray energy into a charge which is amplified by a charge amplifier 106. It should be noted that if the x-ray beam hits a border of the two detector pixels, two detector pixels may receive the x-ray energy which will be converted into two charges. Output of charge amplifier 106 is passed on to the comparator 108, which discriminate the charge into different energy windows (e.g. Low and High energy windows) and provides the corresponding output to the counter 110. The counter 110 then updates (increments) the corresponding low energy or high energy count based on the output from the comparator 108. The contents (or x-ray energy count) of the counter 110 are generally stored in a memory register of the corresponding detector pixel. It should be noted that if there is no charge from the x-ray detector pixel i.e., when no x-ray beam falls on the detector pixel, the counter 110 will not get updated. After a certain time duration (e.g., a recording period time duration), the x-ray energy count of the counter 110 are provided to a processor such as computer 40. Based on the number of counts from multiple counters, the processor finally determines the patient image which may be a bone image or a patient tissue image.

Figure 3:
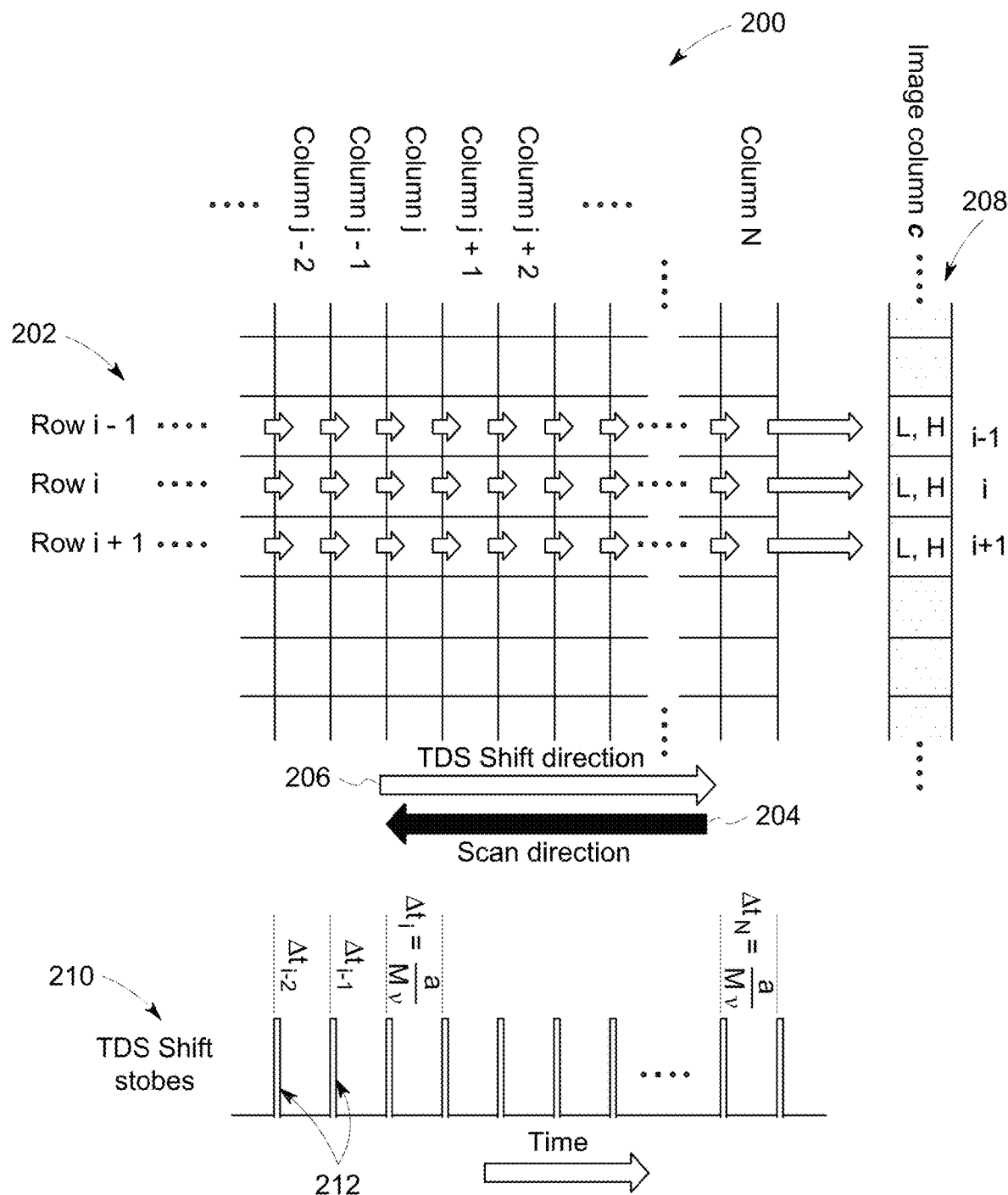
FIG. 3 is a schematic diagram of the Time-Delayed Summation (TDS) technique, in accordance with an embodiment of the present technique.

In the present technique, a Time-Delayed Summation (TDS) technique is used instead of the embodiment shown in FIG. 2. The TDS technique is a process of adding together multiple exposures of the same object as it passes a detector. TDS technique allows images to be taken of moving objects. In the TDS technique, the incremented sums of x-ray energy counts are shifted to a neighboring detector pixel's memory register in synchronization with the x-ray beam motion, such that an object (e.g., a bone) in the scanned subject (e.g., a patient) remains on an x-ray line between a single point in the detector plane and source's focal spot. In the TDS method, this shifting synchronization is dependent on the object's magnification, detector pixel pitch and scan speed. Notably, objects at heights other than the optimum for time-delay synchronization will be blurred since signals through that object will be distributed across multiple points in the detector plane FIG. 3 is a schematic diagram 200 that describes the TDS method in accordance with an embodiment of the present technique. The schematic diagram 200 shows a detector 202 having a detector pixel array of n rows and m columns. As against FIG. 2, where after the recording period time duration, the x-ray energy count of a detector pixel counter is provided to a processor 40, in FIG. 3, the x-ray energy count of the detector pixel counter is shifted to a neighboring detector pixel counter after a TDS shift time duration. For example, in one embodiment, TDS shift time duration may be 0.56 msec and total number of shifts may be 60 for one acquisition whereas the recording period time duration in FIG. 2 may be 6 msec i.e., the recording period time duration may be longer than the TDS shift time duration. The shifting of x-ray energy count from one counter to the next is done for all the detector pixel counters in synchronization with the x-ray beam motion.

For example, if the x-ray scanner is sweeping across the patient and if the scan direction 204 of the x-ray beam is from right to left then the x-ray energy count shift direction 206 is from left to right i.e., opposite direction. A pulse diagram 210 at the bottom of FIG. 3 shows TDS shift strobes or pulses 212 which have a TDS shift frequency f The TDS shift frequency f translates into a TDS shift time duration $\Delta t_0=1/f$ between two pulses. Thus, whenever a TDS shift pulse is received, the counter contents of corresponding detector pixels are shifted to the neighboring counter. As an example, if the TDS shift time duration between two pulses 212 is 1 millisecond (f=1 khz) then the contents of the counter of detector pixel (i, j) are shifted to the right counter of detector pixel (i, j+1) after every 1 millisecond, where i and j corresponds to row number and column number respectively. In other words, the contents of all detector pixel counters corresponding to row i are shifted to their corresponding right column. Moreover, the contents of the last column N are shifted to a main detector memory buffer 208 and then finally to a processor for generating image of the object. In general, by shifting the contents of the counter to the neighboring counter and then adding them together, multiple x-rays passing through a bone of the patient are integrated as the x-ray beam passes through that bone over a given time duration. The TDS shift frequency f depends on a plurality of parameters such as a velocity v of the x-ray source motion and will be explained in more detail in subsequent paragraphs.

Figure 4:
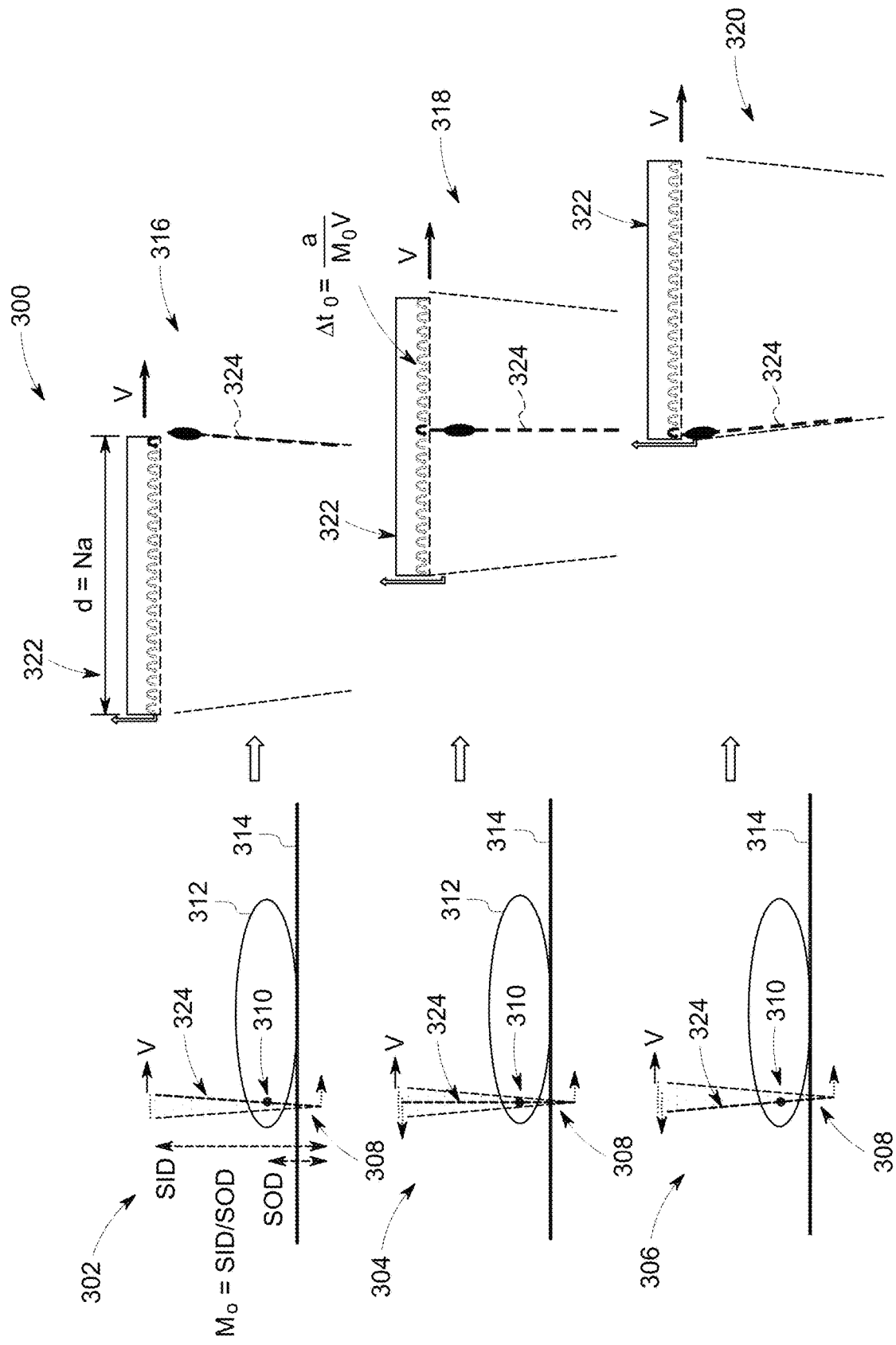
FIG. 4 is a schematic diagram depicting a TDS imaging sequence of a bone of a patient, in accordance with an embodiment of the present technique.

FIG. 4 is a schematic diagram 300 depicting TDS imaging sequence of a bone of a patient. Schematic diagram 300 shows three steps 302, 304, 306 of TDS imaging sequence corresponding to 3 positions of the X-ray beam 308 at three different time instances. Schematic diagram 300 shows an object e.g., a bone 310 in a patient 312 who is lying on a table 314. For all three steps 302, 304, 306, corresponding positions 316, 318, 320 of detector 322 are also shown in schematic diagram 300. The detector 322 includes N number of detector pixel columns, each pixel having dimension α. Thus, the total detector width d equals d=Nα.

When the x-ray scanner is sweeping across the patient, step 302 is the first time instance when the x-ray beam 308 passes through the bone 310. In the embodiment shown, the x-ray scanner is moving from left side to the right side in reference to the bone 310 at a velocity v. Thus, at step 302, the x-ray beam 308 is at an acute angle with respect to table plane 314 to start with. The attenuated x-ray beam 324 i.e., the x-ray beam 308 after passing through the bone 310 then hits the first detector pixel of the detector 322 as seen in detector position 316. Step 304 refers to a second time instance when the x-ray beam 308 is at a right angle with respect to table plane 314. The attenuated x-ray beam 324 then hits the middle detector pixel of the detector 322 as seen in detector position 318. Step 306 corresponds to a third time instance when the x-ray beam 308 is at an obtuse angle with respect to table plane 314. In this instance, the attenuated x-ray beam 324 hits the last detector pixel as seen in detector position 320.

If the TDS method is not used then the charge accumulated at detector pixels corresponding to bone imaging at positions 316, 318 and 320 would remain at the same detector pixels i.e., first, middle and last detector pixel. This would result in bone image being distributed across the whole detector and so the final bone image would be blurry. Alternatively, the frame rate could be increased to reduce blurring, at the cost of increasing data volume and re-registration of frame in image reconstruction. However, in the TDS method, the contents of detector pixels are continuously shifted to the neighboring pixel counter at a TDS shift frequency till the bone is completely imaged and finally the charge corresponding to bone image at positions 316, 318 and 320 gets accumulated in a last detector pixel. The contents of the last detector pixels are then read out by the processor for generating the bone image. In other words, bone image charge at all the detector positions gets integrated in one detector pixel instead of getting distributed across the entire detector resulting in a less-blurry or clearer image of the bone.

In one embodiment, the TDS shift frequency is synchronized with the x-ray beam motion and is given as $$f = \frac{M_O v}{a} \quad (1)$$

where v is the scanning speed or x-ray beam motion speed, a is the detector pixel dimension in the shift direction, and $M_O$ is the magnification factor of the object i.e., bone. The magnification factor depends on the distance of the bone away from the source. For example, the closer the bone is to the source, the greater the magnification of that bone on the detector plane. In general, the magnification factor Mo of the object is given as an x-ray source to image distance (SID) divided by the x-ray source to object distance (SOD) i.e., $$M_O = SID/SOD \quad (2)$$

The image is measured in the detector plane so the x-ray source to image distance can also be considered as source to detector distance. It can be seen from equation (1) above that the TDS shift frequency (i.e., the frequency at which the contents of the detector pixel counters are shifted to the neighboring detector pixel counter) depends on the distance between the object and the x-ray source i.e., SOD. So, if a wrong SOD is used while determining the TDS shift frequency then the content of the detector pixel counter won't be shifted in perfect synchronization with the x-ray beam motion resulting in a sub-optimal image of the bone.

Figure 5:
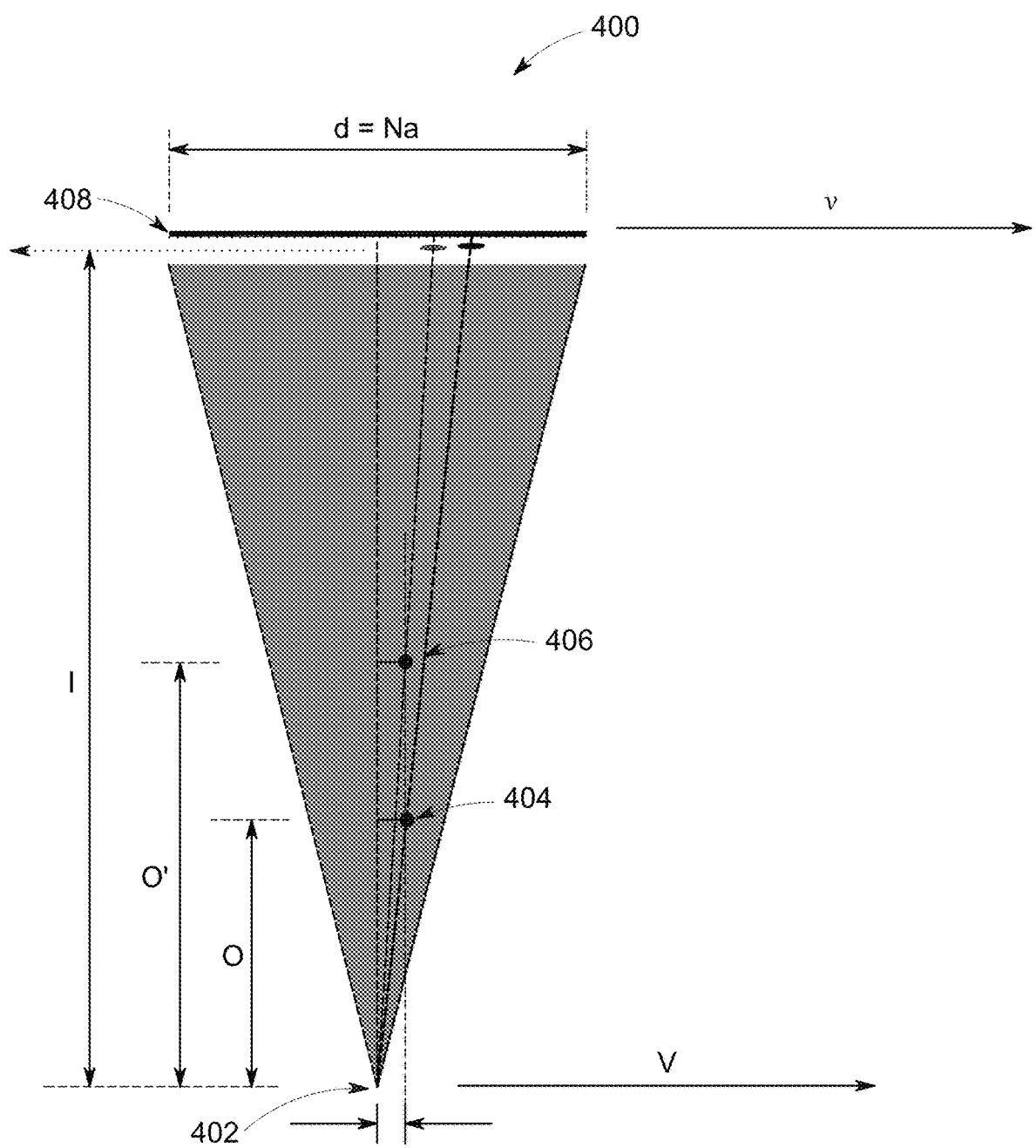
FIG. 5 is a schematic diagram depicting effect of TDS imaging on objects having different heights, in accordance with an embodiment of the present technique.

FIG. 5 is a schematic diagram 400 depicting effect of TDS imaging on objects having different heights. The schematic diagram 400 shows x-ray source 402 and a detector 408. A first object 404 is located at a distance O from source 402 and a second object 406 is located at a distance O' from source 402. Further, the detector 408 or the image plane is located at a distance equal to I from the source 402 i.e., SID=I. In this case, if the optimum TDS shift frequency is set based on object 404 (i.e., SOD=O in equation (2) above) then the x-ray energy count of the detector pixels corresponding to object 404 would shift to neighboring pixel counters in the same row. Thus, the shifting would happen in synchronization with the x-ray beam motion but in an opposite direction of movement of the x-ray beam motion. This results in a less blurry image of the object 404.

Because object 406 is at a different height compared to object 404, the x-ray energy count corresponding to object 406 would not shift to neighboring pixel counters in synchronization with the x-ray beam motion. In other words, the shifting of x-ray energy count corresponding to object 406 to the neighboring pixel counter may fall behind the speed of the x-ray beam motion resulting in a slippage of the image of object 406 for every TDS shift time duration Δt=1/f. In one embodiment, the image slippage (s) of object 406 per TDS shift time duration may be given as:

$$s = a \frac{o - o'}{o'} \quad (3)$$

It should be noted that this slippage is independent of velocity v and there is no transverse bias in the position. In an example, assume that I=73 cm, O=20 cm, and O'=30 cm, α=0.2 mm and N=32. In this case, in the detector plane, the total TDS blurring of object 406 at O' would be sN=2.1 mm, compared to pixelation and motion blurring of mm for object 404 at O which is optimally synchronized. Thus, it can be seen that knowing the height of the object is very important in determining the optimal TDS shift frequency for capturing the best image of the object.

Referring back to FIG. 1, in one embodiment, the acquired images from system as described above are further used to measure, for example, bone mineral density (BMD) or other bone and tissue characteristics or content. In one embodiment, the system involves two X-ray beams with differing energy levels that are directed toward a target bone for measurement. In a preferred embodiment, a single multi-spectral x-ray beam is used. After soft tissue absorption is subtracted out of the x-ray image, BMD can be determined from the absorption of each beam by bone. In another embodiment, the two images corresponding to the two energy levels (i.e., high and low) are aligned and mathematically combined to produce the necessary bone density information according to mathematical algorithms known in the art (e.g. basis set material decomposition). The system 10 uses the TDS technique described above to acquire object images. However, the height of the object needed to determine the optimal TDS shift frequency is generally not known in advance. In one embodiment, the height of the object is an estimate based on prior data. The prior data may be historical data of the same object or data of similar objects obtained in past.

In another embodiment, the technique presented herein first determines the height of the object and then accordingly determines the optimal TDS frequency. For example, in one embodiment, the object height determination technique as described in patent U.S. Pat. No. 6,081,582 is utilized. The U.S. Pat. No. 6,081,582 is incorporated by reference herein for object height determination purpose and adjacent scan image merging purpose. In general, the object height is determined based on adjacent scan images which are the result of use of a fan beam in transverse scan as explained with respect to FIG. 6. It should be noted that the while describing TDS technique in FIG. 4 above, only one sweep of the scanner over an object was considered and how the charge data for that sweep is integrated was explained. On the contrary, FIG. 6 described below corresponds to a transverse scan of the object. For transverse scan, the x-ray source and the x-ray detector are moved in a raster pattern (FIG. 1) so as to trace a series of scans of the patient during which dual energy x-ray data is collected by the x-ray detector 26.

Figure 6:
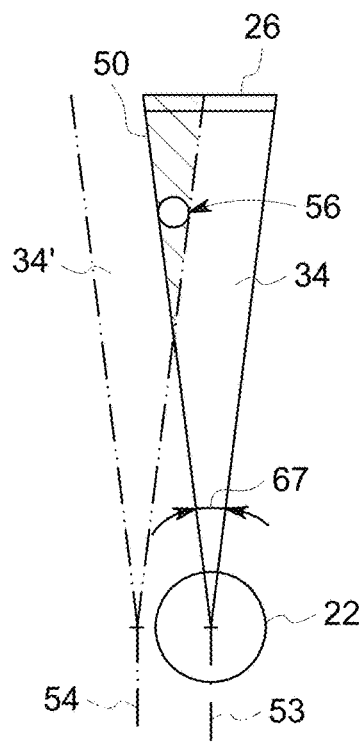
FIG. 6 is a schematic diagram of the x-ray source and linear detector of FIG. 1 showing the divergence angle of a fan beam of radiation and a region of overlap in the fan beam for adjacent scan images, in accordance with an embodiment of the present technique.

Referring now to FIG. 6, the fan beam 34 of system 10 diverges slightly (e.g., with a divergence angle 67) as it passes from a focal spot of the x-ray source 22 to the detector 26. This creates a triangular overlap region 50 formed by the intersection of the volumes of the swept fan beams for successive transverse scans. Generally, the overlap region 50 is formed by the intersection of the area of the fan beam 34 when the x-ray source and detector 26 are in a first position 52 to acquire a first scan image and the area of the fan beam 34' when moved to an adjacent second longitudinal position 54 to acquire a second scan image. As will be appreciated by those skilled in the art, overlap between adjacent scans distorts or blurs the imaged produced by combining the scan images near the edges of the scan images. The blurring is caused by a dependency of the projected image on the height of the imaged structure (the "height dependency problem") that displaces the relative position of the structure in the two scan image as a result of the different angles of illumination of the structure by the adjacent beams of radiation. In the present invention, the fan beam 34 is collimated to reduce this divergence to a value of less than 10° and preferably to approximately 4° so as to reduce parallax and height dependency problems. The increased numbers of overlap regions 50 required by the small fan beam angle are rendered acceptable by the reduced parallax of the beams and additional imaging processing steps to be described.

Figure 7:
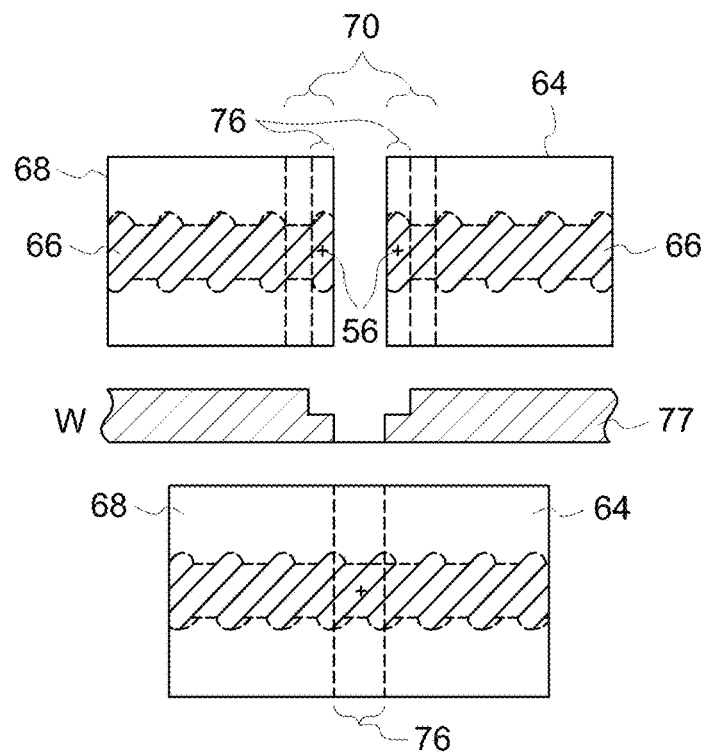
FIG. 7 is a schematic diagram of two scanned images before and after merging, in accordance with an embodiment of the present technique.

Referring now to FIG. 7, a first scan image 64 may be obtained with a transverse scan such as that at first longitudinal position 53 as shown in FIG. 6 and shows an object 56, in this case, a portion of a spinal column 66 that is also imaged in a second scan image 68 acquired along second longitudinal position 54 as shown in FIG. 6. Adjacent edges of scan images 64 and 68 have overlap portions 70 that are known functions of the size of the raster scan (the longitudinal increment) and the known divergence of the fan beam 34. Nevertheless, the exact position of objects 56 within the overlap portion 70 of images 68 and 66 will vary depending on the height of the object 56. Accordingly, images 68 and 64 must be shifted longitudinally with respect to each other to overlap by an arbitrary amount to bring objects 56 into alignment.

Figure 8:
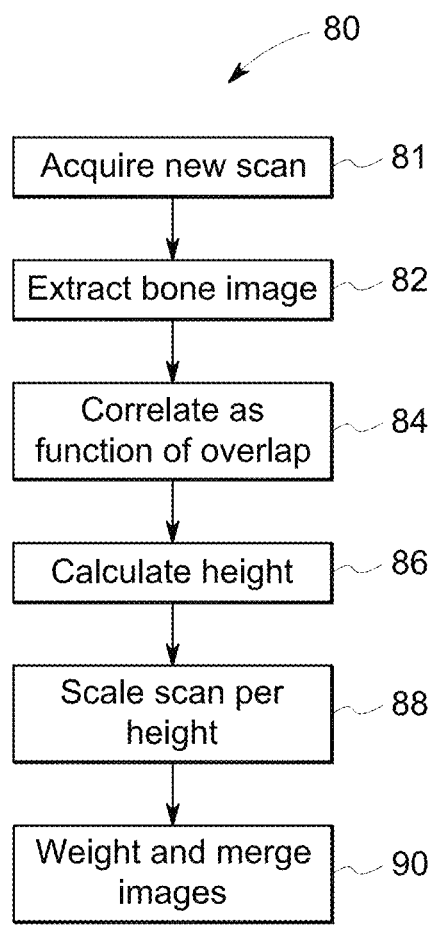
FIG. 8 is a flowchart describing a method of merging adjacent scan images of FIG. 7, in accordance with an embodiment of the present technique.

FIG. 8 shows a flowchart 80 describing a method of merging adjacent scan images of an object generated due to overlap between adjacent scans. In step 81, the present invention acquires successive transverse scans to produce scan images 64 and 68 having overlap portions 70 as shown in FIG. 7. At a succeeding step 82, an object image or a bone image is extracted from each of the scan images 64 and 68 so as to highlight the image of the object or bone 56 of relevance in the measurement. At step 84, the data of the adjacent scan images 64 and 66 within the overlap portions 70 are then correlated for a series of overlaps of progressively greater longitudinal amount to deduce an optimal or best fit overlap for the particular imaged object 56. Optimal overlap occurs when adjacent sweeps image the same region of bone in their respective overlap regions. Therefore, optimal overlap is determined by minimizing the difference in estimated bone in each sweep's overlap region. It will be recognized that to the extent that imaged object 56 has varying or multiple height within the overlap portions 70, this best fit will in fact reflect an average of that height.

The height of the bone itself is calculated at step 86 using simple trigonometric identities relying on the known beam angle 67 and a longitudinal distance D of the overlap region 50 determined from the overlap images. For example, a triangle is formed with base D, height as H and the beam angle 67. Thus, if the beam angle and base is known then height H can be calculated using trigonometric principles. This height is used at step 88 to scale the image 64 or 68 so as to provide a predetermined constant magnification to the object 56. This correction for scaling provides increased accuracy to quantitative uses of the data, for example, in density measurements and provides improved merging of the image data to the extent that both images have similar magnification. Finally, at step 90, images are weighted with the weighting mask 77 shown in FIG. 7 and merged to create to a single file of image data.

Figure 9:
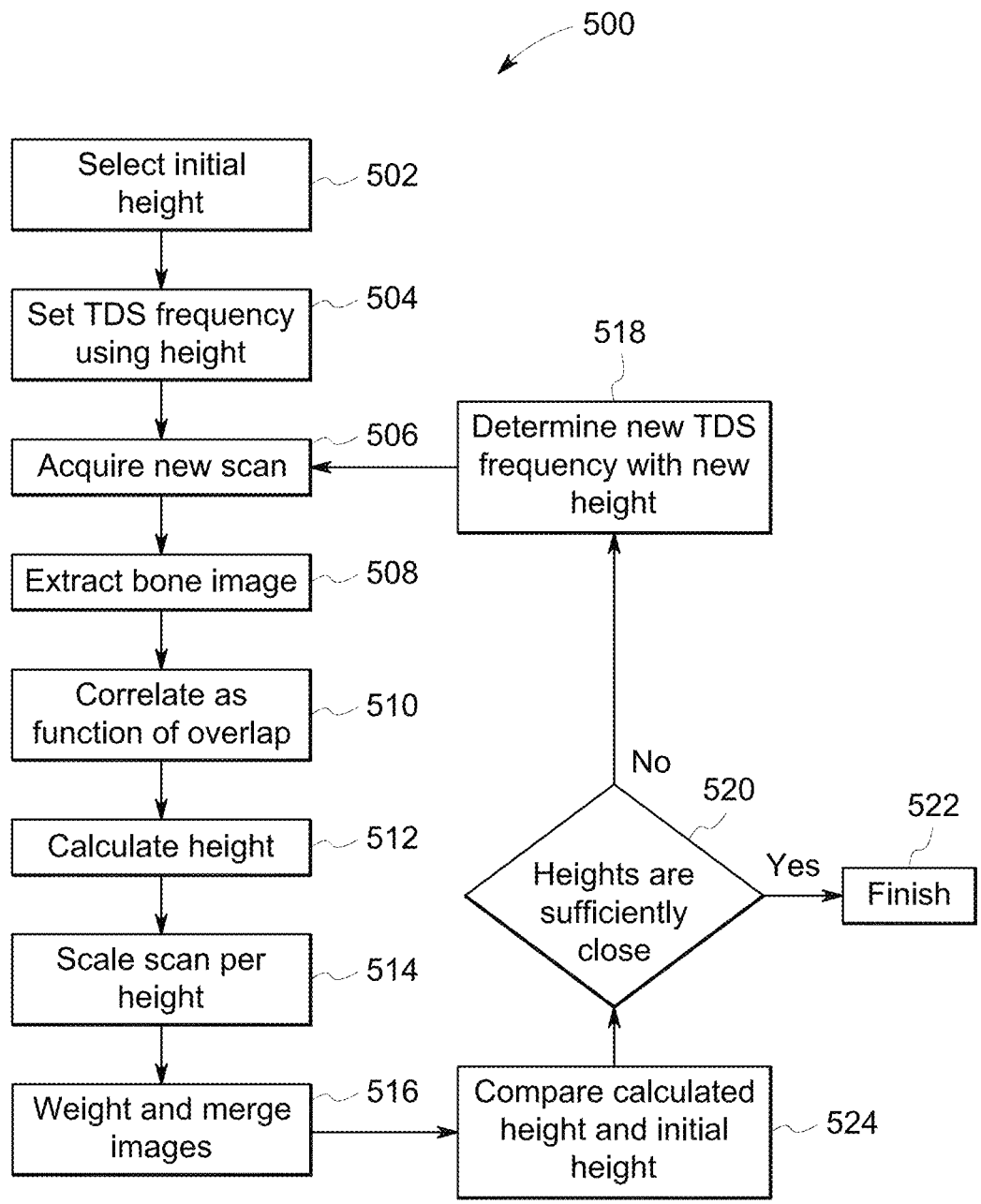
FIG. 9 is a flowchart describing a method of imaging a patient, in accordance with an embodiment of the present technique.

FIG. 9 shows a flowchart 500 describing a method of imaging a patient in accordance with an embodiment of the present technique. In step 502, the method includes selecting an initial height of the bone with respect to the x-ray source level. Selecting the initial height of the bone may include making an estimate based on prior data. The prior data may be historical data of the same patient or data of similar objects obtained in past. For example, the femur may be 5 cm deep inside the body based on historical averages for that body type. But for a particular patient, previous measurements may have shown that femur height is an extra 5 cm higher, so then the height of the femur may be selected as 10 cm. Further, if the distance from the body of the patient to the X-ray source level is another cm then the height may be selected as 10+10=20 cm.

In step 504, TDS frequency is determined based on the initial height of the patient bone. The TDS frequency may be determined as in equation (1) above. Thereafter, steps 506-516 which are similar to steps 81-90 of FIG. 8 are performed. In other words, in steps 506, successive transverse scans of the patient are acquired based on the TDS frequency. The transverse scan generates scan images of the bone having overlap portions. A bone image is then extracted from each of the scan images in step 508. At step 510, the data of the adjacent scan images within the overlap portions are correlated. The height of the bone is calculated at step 512. This height is used at step 514 to scale the scan images so as to provide a predetermined constant magnification to the bone. Finally, at step 516, scan images are weighted with the weighting mask and merged to generate the bone image.

At step 524, the calculated height of the bone in step 512 is compared with the initial height in step 502. At step 520 it is determined if the initial height is sufficiently close with the calculated height. In one embodiment, a threshold value may be used to determine whether the initial and calculated heights are sufficiently close. In one embodiment, such a threshold may be 1 cm. In another embodiment, such a threshold may be 2 cm and so on. If the heights are not sufficiently close, then the method moves to step 518 where a new TDS frequency is determined based on the calculated height of the bone in step 512. The method then moves back to step 506 to repeat the scan and to generate the new bone image based on the new TDS frequency determined in step 518. However, if in step 518, it is determined that the initial height is sufficiently close to the calculated height then the scan is finished in step 522 which finalizes the bone image.

Figure 10:
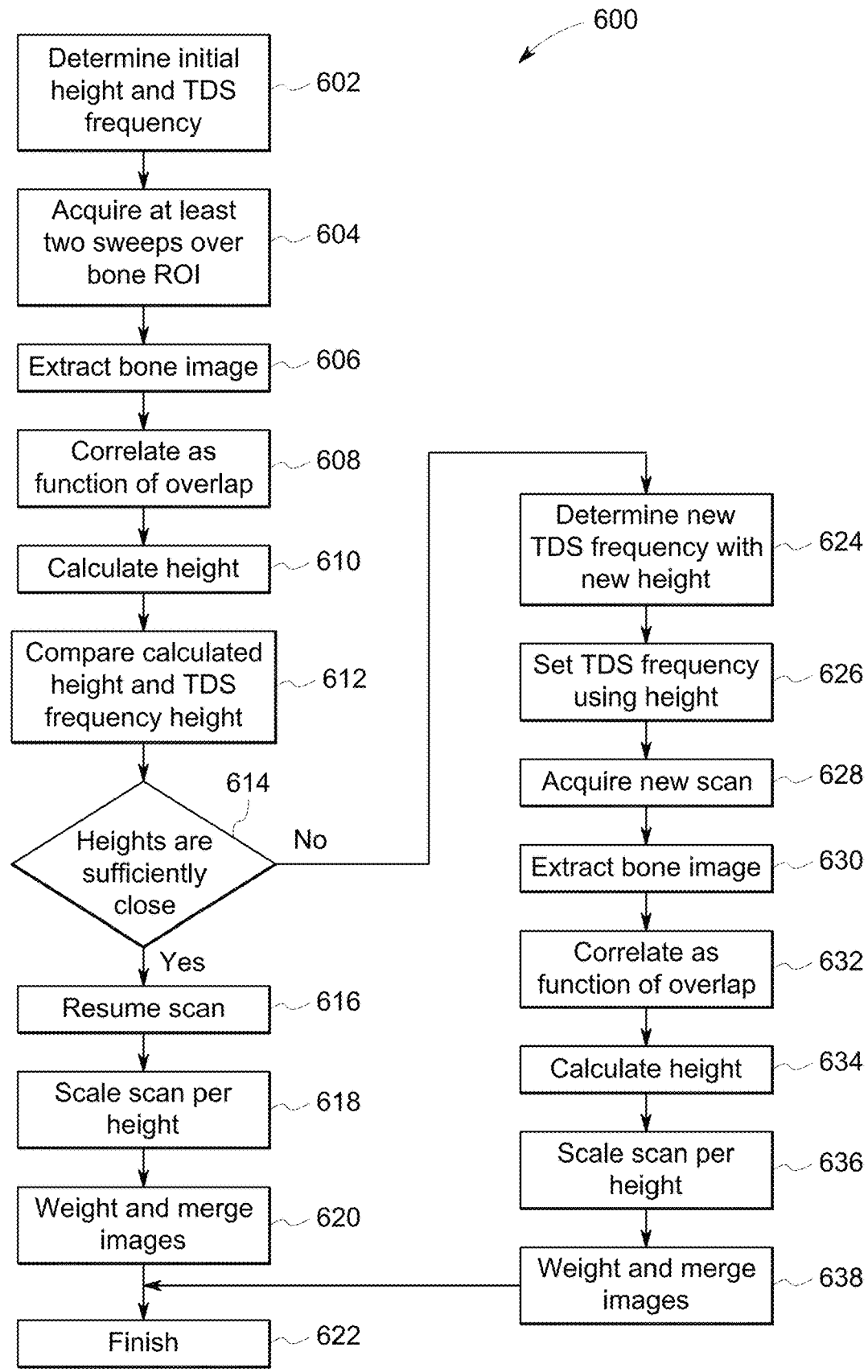
FIG. 10 is a flowchart describing another method of imaging a patient, in accordance with an embodiment of the present technique.

FIG. 10 shows a flowchart 600 describing another method of imaging a patient in accordance with an embodiment of the present technique. As earlier, at start, an initial height of the bone with respect to the x-ray source level is determined in step 602. Based on the initial height, the TDS frequency is also determined in step 602 based on equation (1). As against FIGS. 8 and 9, in this method, a complete scan of the bone is not performed based on the TDS frequency. Instead, at step 604, based on the TDS frequency at least two or three sweeps of the x-ray source over the bone region of interest are carried out to generate scan images of the bone having overlap portions. In steps 606, a bone image is extracted from each of the scan images. At step 608, the data of the adjacent scan images within the overlap portions are correlated. The height of the bone is calculated at step 610.

At step 612, the calculated height of the bone in step 610 is compared with the initial height in step 602. At step 614 it is determined if the initial height is sufficiently close with the calculated height. If the heights are not sufficiently close, then the method moves to step 624 where a new TDS frequency is determined based on the calculated height of the bone in step 610 and the new TDS frequency is set up in the system in step 626. The method then continues to steps 628-638 which are similar to steps 81-90 of FIG. 8 and are performed similarly to generate the final bone image of the patient.

However, if at step 614 it is determined that the initial height selected in step 602 is sufficiently close to the calculated height in step 610 then the method moves to step 616 to resume the scan. At step 618, the calculated height is used to scale the scan images generated in step 604 so as to provide a predetermined constant magnification to the bone. Finally, at step 620, scan images are weighted with the weighting mask and merged to generate the bone image and the method is ended at step 622.

Figure 11:
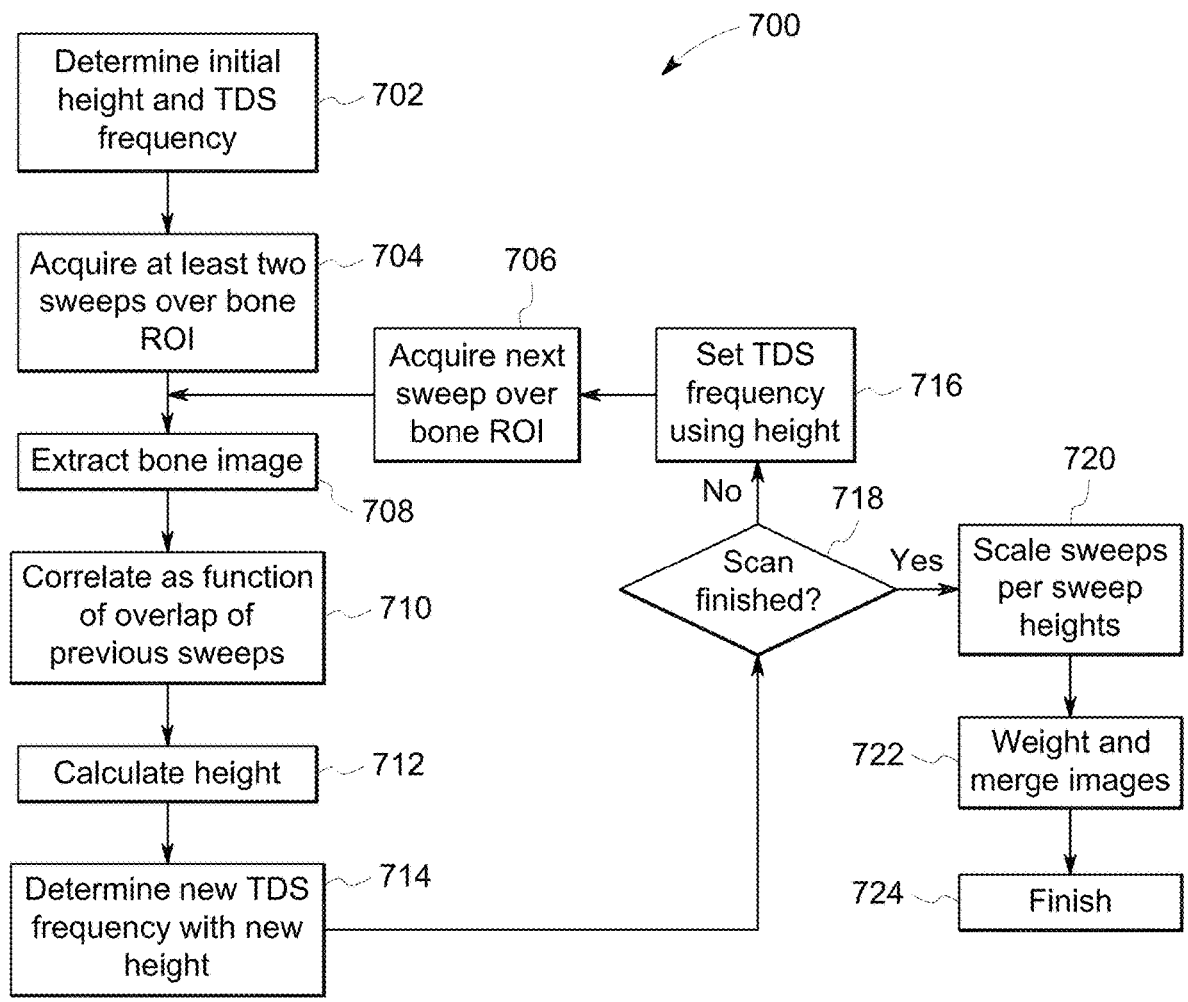
FIG. 11 is a flowchart describing yet another method of imaging a patient, in accordance with an embodiment of the present technique.

FIG. 11 shows a flowchart 700 describing yet another method of imaging a patient in accordance with an embodiment of the present technique. Similar to method 600, at start, an initial height of the bone with respect to the x-ray source level is determined in step 702. Based on the initial height, the TDS frequency is also determined in step 702. However, the main difference between method 600 and method 700 is that in method 700, the TDS frequency is adjusted after every sweep of the x-ray source over the bone region of interest. For example, at step 704, based on the TDS frequency-at least two initial sweeps of the x-ray source over the bone region of interest is carried out to generate scan images of the bone having overlap portions. In steps 708, a bone image is extracted from each of the scan images. At step 710, the data of the adjacent scan images within the overlap portions is correlated. As described earlier, the height of the bone is calculated at step 712. Based on the height determined in step 712, a new TDS frequency is determined in step 714.

At step 718, it is determined whether the scan is completed or not. It should be noted that the scan is completed when last sweep has been acquired. All scans have a user-prescribed length to cover the site of interest. This scan length determines a fixed number of sweeps for the scan. Thus, if the last sweep of the fixed number of sweeps is not completed, then the new TDS frequency is set up in the system in step 716. Based on the new TDS frequency, at step another sweep of the x-ray source over the bone region of interest is carried out. The method then continues to step 708 as earlier. However, if at step 718 it is determined that the scan is complete then at step 720, the calculated height in step 712 is used to scale the scan images generated in step 704 or 706. Finally, at step 722, scan images are weighted with the weighting mask and merged to generate the bone image and the method is ended at step 724.

Figure 12:
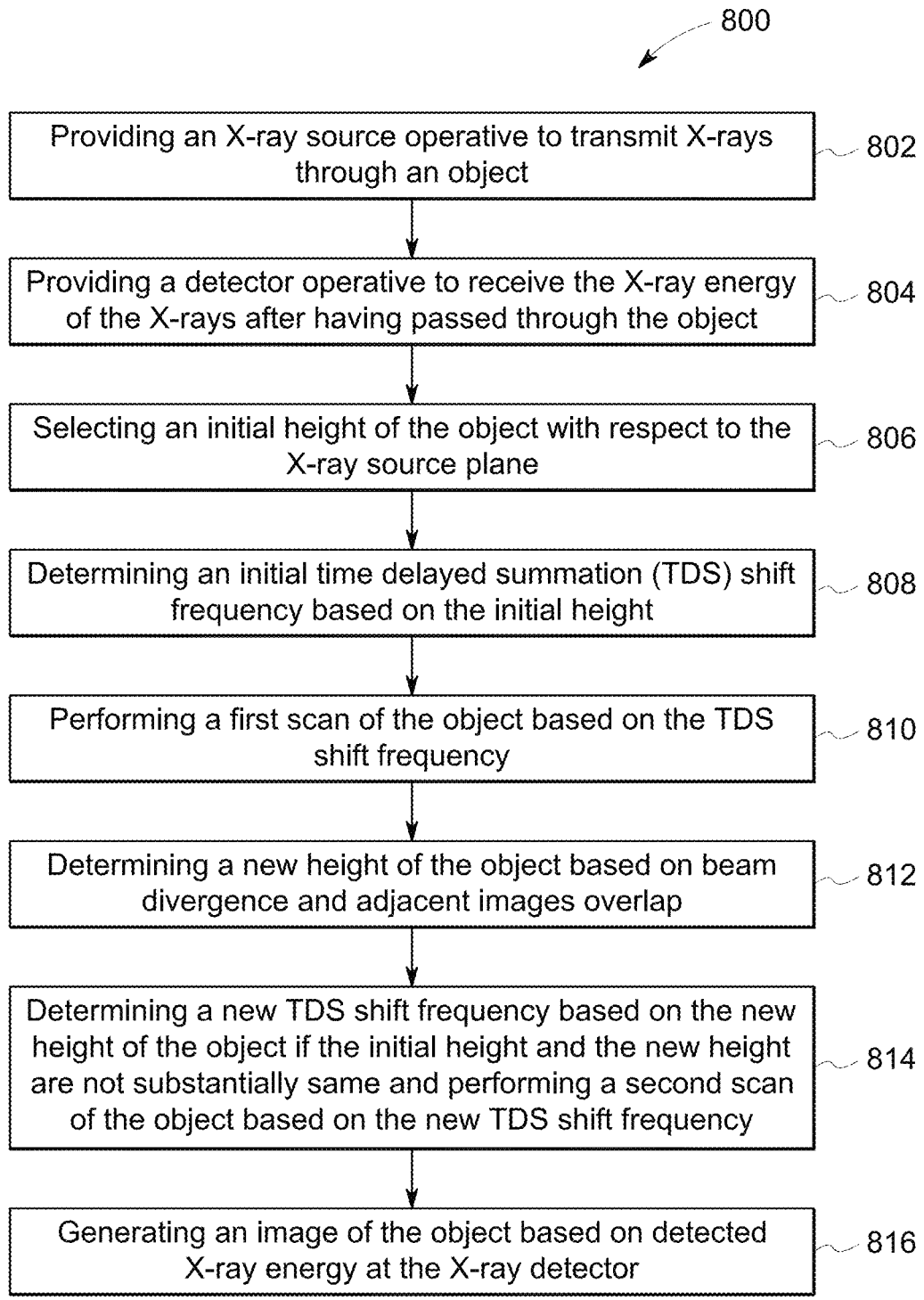
FIG. 12 is a flowchart describing a method of imaging a patient in accordance with yet another embodiment of the present technique.

FIG. 12 shows a flowchart 800 describing a method of imaging a patient in accordance with another embodiment of the present technique. At step 802, an X-ray source is provided which is operative to transmit X-rays through an object. The X-ray source is collimated to produce a diverging beam of radiation. In one embodiment, the X-ray source may operate in a single energy mode or a dual energy mode. At step 804, the method includes providing a detector which is operative to receive the X-ray energy of the X-rays after having passed through the object. In one embodiment, the detector may be embodied as either a linear array of detector elements, a side linear array of detector elements, which includes two transversely separated rows of detector elements, or a stacked array detector in which the detector elements are stacked along a direction of propagation of the radiation and are selectively sensitive to low and high energy spectrums, respectively. The method further includes, selecting an initial height of the object with respect to the X-ray source plane at step 806. Selecting the initial height of the bone may include making an estimate based on prior data. The prior data may be historical data of the same patient or data of similar objects obtained in past.

At step 808, the method includes determining an initial time delayed summation (TDS) shift frequency based on the initial height. In general, TDS shift frequencies depend on x-ray beam motion speed, a detector pixel dimension, and a magnification factor of the object on the detector, wherein the magnification factor of the object depends on the height of the object. Based on the initial TDS shift frequency a first scan of the object is performed in step 810. Further, at step 812, a new height of the object is determined based on beam divergence characteristics and adjacent images overlap. The adjacent images are result of intersection of a first area of an x-ray fan beam when the x-ray source and the detector are in a first position and a second area of the x-ray fan beam when the x-ray source and the detector are in a second position.

If the initial height and the new height are not substantially same then at step 814, a new TDS shift frequency based on the new height is determined and a second scan based on the new TDS shift frequency is performed. Finally, at step 816, an image of the object based on detected X-ray energy at the X-ray detector is generated.

In one embodiment of the method 800, the first scan of the object includes performing only a couple of x-ray source sweeps across the object and the second scan of the object includes a full scan of the object. In this specific embodiment, remaining x-ray source sweeps of the first scan are performed if the initial height and the new height are substantially same. In another embodiment, the first scan and the second scan are both full scan of the object. In yet another embodiment, the first scan and the second scan are both single x-ray sweeps of the object and the steps are repeated till the complete scan is over.

In the event of inconsistent usages between this document and those documents so incorporated by reference, the usage in the incorporated reference(s) should be considered supplementary to that of this document; for irreconcilable inconsistencies, the usage in this document controls.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112(f). However, for any claims containing elements designated in any other manner, it is intended that such elements are not to be interpreted under 35 U.S.C. 112(f).

This written description uses examples to disclose the present subject matter, including the best mode, and also to enable any person skilled in the art to practice the subject matter, including making and using any devices or systems and performing any incorporated methods. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A medical imaging system comprising:
    an X-ray source operative to transmit X-rays through an object, wherein the X-ray source is collimated to produce a diverging beam of radiation;
    a detector operative to receive the X-ray energy of the X-rays after having passed through the object, wherein the detector includes detector pixels arranged in at least one row; and
    a processing system programmed to:
        select an initial height of the object with respect to the X-ray source plane;
        determine an initial time delayed summation (TDS) shift frequency based on the initial height;
        perform a first scan of the object based on the TDS shift frequency;
        determine a new height of the object based on a beam angle and an overlap of adjacent images;
        determine a new TDS shift frequency based on the new height of the object if the initial height and the new height are not substantially same and perform a second scan of the object based on the new TDS shift frequency; and
        generate an image of the object based on detected X-ray energy at the X-ray detector based on the first scan and the second scan.

2. The medical imaging system of claim 1, wherein each scan of the object includes a plurality of sweeps across the object and during each sweep, x-ray energy count values of the detector pixels are shifted by one pixel and contents of the last detector pixel in the row are shifted to a main buffer.

3. The medical imaging system of claim 2, wherein the shifting and summing of x-ray energy count values is performed at the respective TDS shift frequency and the shifting is performed in a direction opposite to the direction of the movement of the detector.

4. The medical imaging system of claim 1, wherein the first scan of the object includes performing only a couple of x-ray source sweeps across the object and the second scan of the object includes a full scan of the object.

5. The medical imaging system of claim 4, wherein the processing system is further programmed to perform remaining x-ray source sweeps of the first scan if the initial height and the new height are substantially same be.

6. The medical imaging system of claim 1, wherein the first scan and the second scan are both full scan of the object.

7. The medical imaging system of claim 1, wherein the first scan and the second scan are both two x-ray sweeps of the object.

8. The medical imaging system of claim 1, wherein both the initial and the new TDS shift frequencies depend on x-ray beam motion speed, a detector pixel dimension, and a magnification factor of the object on the detector, wherein the magnification factor of the object depends on the height of the object.

9. The medical imaging system of claim 1, wherein the adjacent images are result of intersection of a first area of an x-ray fan beam when the x-ray source and the detector are in a first position and a second area of the x-ray fan beam when the x-ray source and the detector are in a second position.

10. The medical imaging system of claim 9, wherein the processing system is further programmed to scale the adjacent images according to the new height of the object.

11. The medical imaging system of claim 10, wherein the processing system is further programmed to weigh the scaled adjacent image and merged to weighed images to a single image.

12. The medical imaging system of claim 1, wherein the object is a bone of a patient and the processing system is further programmed to repeat the first and the second scan for remaining portion of the patient.

13. A method for imaging an object comprising:
    providing an X-ray source operative to transmit X-rays through an object, wherein the X-ray source is collimated to produce a diverging beam of radiation;

providing a detector operative to receive the X-ray energy of the X-rays after having passed through the object;

selecting an initial height of the object with respect to the X-ray source plane;

determining an initial time delayed summation (TDS) shift frequency based on the initial height;

performing a first scan of the object based on the TDS shift frequency;

determining a new height of the object based on a beam angle and adjacent images overlap;

determining a new TDS shift frequency based on the new height of the object if the initial height and the new height are not substantially same and performing a second scan of the object based on the new TDS shift frequency; and generating an image of the object based on detected X-ray energy at the X-ray detector based on the first scan and the second scan.

14. The method for imaging the object of claim 13, wherein each scan of the object includes a plurality of sweeps across the object and during each sweep, x-ray energy count values of the detector pixels are shifted by one pixel and contents of the last detector pixel in the row are shifted to an image counter.

15. The method for imaging the object of claim 14, wherein the shifting and summing of x-ray energy count values is performed at the respective TDS shift frequency and the shifting is performed in a direction opposite to the direction the movement of the detector.

16. The method for imaging the object of claim 13, wherein the first scan of the object includes performing only a couple of x-ray source sweeps across the object and the second scan of the object includes a full scan of the object.

17. The method for imaging the object of claim 16 further comprising performing remaining x-ray source sweeps of the scan if the initial height and the new height are substantially same.

18. The method for imaging the object of claim 13, wherein the first scan and the second scan are both full scan of the object.

19. The method for imaging the object of claim 13, wherein the first scan and the second scan are both single x-ray sweeps of the object.

20. The method for imaging the object of claim 13, wherein both the initial and the new TDS shift frequencies depend on x-ray beam motion speed, a detector pixel dimension, and a magnification factor of the object on the detector, wherein the magnification factor of the object depends on the respective height of the object.

* * * * *